(12) United States Patent
Shintou et al.

(10) Patent No.: US 8,951,340 B2
(45) Date of Patent: Feb. 10, 2015

(54) WATER-INSOLUBLE COLORING MATTER COMPOUND, INK USING THE WATER-INSOLUBLE COLORING MATTER COMPOUND, THERMAL TRANSFER RECORDING SHEET AND RESIST COMPOSITION FOR COLOR FILTER

(71) Applicant: Canon Kabushiki Kaisha, Tokyo (JP)

(72) Inventors: Taichi Shintou, Saitama (JP); Takayuki Ujifusa, Ashigarakami-gun (JP); Masao Nakano, Kamakura (JP); Yutaka Tani, Yokohama (JP); Satoshi Saito, Mishima (JP); Takeshi Miyazaki, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/239,456

(22) PCT Filed: Oct. 2, 2012

(86) PCT No.: PCT/JP2012/076057
§ 371 (c)(1),
(2) Date: Feb. 18, 2014

(87) PCT Pub. No.: WO2013/051724
PCT Pub. Date: Apr. 11, 2013

(65) Prior Publication Data
US 2014/0205773 A1 Jul. 24, 2014

(30) Foreign Application Priority Data

Oct. 4, 2011 (JP) ................................. 2011-219866

(51) Int. Cl.
*C09D 11/00* (2014.01)
*C09B 5/14* (2006.01)
(Continued)

(52) U.S. Cl.
CPC .............. *C07D 221/18* (2013.01); *C09D 11/00* (2013.01); *C09B 5/14* (2013.01);
(Continued)

(58) Field of Classification Search
CPC ......... C09D 11/00; C09D 11/328; C09B 5/14

USPC .......................................... 106/31.47; 546/76
See application file for complete search history.

(56) References Cited

U.S. PATENT DOCUMENTS 3,076,808 A 2/1963 Blout et al.
3,126,280 A 3/1964 Blout et al.
(Continued)

FOREIGN PATENT DOCUMENTS

GB 903590 A 8/1962
JP 7-232481 A 9/1995
(Continued)

*Primary Examiner* — Helene Klemanski
(74) *Attorney, Agent, or Firm* — Fitzpatrick, Cella, Harper & Scinto

(57) ABSTRACT

An object of the present invention is to provide a water-insoluble coloring matter compound having high solubility for a solvent and high lightness and chroma and providing a chromaticity closer to the magenta chromaticity represented by the Adobe RGB color space. A water-insoluble coloring matter compound represented by the formula (1) is provided:

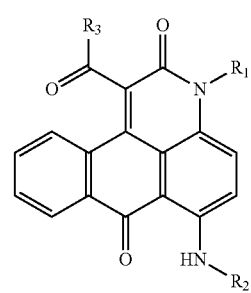

Formula (1)

wherein $R_1$ and $R_2$ represent an alkyl group, and $R_3$ represents an alkyl group, an aryl group, or an alkoxy group. And the alkyl group, the aryl group and the alkoxy group regarding to $R_1$ to $R_3$ are capable of having a substituent.

6 Claims, 1 Drawing Sheet

(51) Int. Cl.
 *C07D 221/18* (2006.01)
 *C09D 11/037* (2014.01)
 *C09D 11/322* (2014.01)

(52) U.S. Cl.
 CPC ........... *C09D 11/037* (2013.01); *C09D 11/322* (2013.01)
 USPC .......................................... 106/31.47; 546/76

(56) References Cited

U.S. PATENT DOCUMENTS

| | | | |
|---|---|---|---|
| 3,376,320 A | 4/1968 | Schwander et al. | |
| 3,455,969 A | 7/1969 | Schwander et al. | |
| 3,462,463 A | 8/1969 | Schwander et al. | |
| 3,728,113 A | 4/1973 | Becker et al. | |
| 4,740,581 A * | 4/1988 | Pruett et al. | 546/76 |
| 5,602,073 A | 2/1997 | Harada | |
| 6,152,969 A * | 11/2000 | Matsumoto et al. | 546/76 |
| 6,706,102 B2 * | 3/2004 | Blease et al. | 106/31.47 |
| 7,211,131 B2 * | 5/2007 | Banning et al. | 106/31.29 |
| 7,297,196 B2 * | 11/2007 | Matsumoto et al. | 106/31.47 |
| 7,828,886 B2 * | 11/2010 | Baettig et al. | 106/31.47 |
| 2011/0189096 A1 | 8/2011 | Watanabe et al. | |
| 2011/0236310 A1 | 9/2011 | Watanabe et al. | |
| 2013/0280169 A1 | 10/2013 | Watanabe et al. | |
| 2014/0113229 A1 * | 4/2014 | Tani et al. | 430/108.21 |
| 2014/0113231 A1 * | 4/2014 | Shintou et al. | 106/31.77 |
| 2014/0162182 A1 * | 6/2014 | Nakano et al. | 430/108.21 |
| 2014/0225048 A1 * | 8/2014 | Saito et al. | 252/586 |

FOREIGN PATENT DOCUMENTS

| | | |
|---|---|---|
| JP | 2003-005361 A | 1/2003 |
| JP | 2004-292572 A | 10/2004 |
| JP | 2005-162938 A | 6/2005 |
| JP | 2005-320480 A | 11/2005 |
| JP | 2011-116852 A | 6/2011 |
| WO | 2013/015433 A1 | 1/2013 |
| WO | 2013/015434 A1 | 1/2013 |
| WO | WO 2013/015433 A1 * | 1/2013 |

* cited by examiner

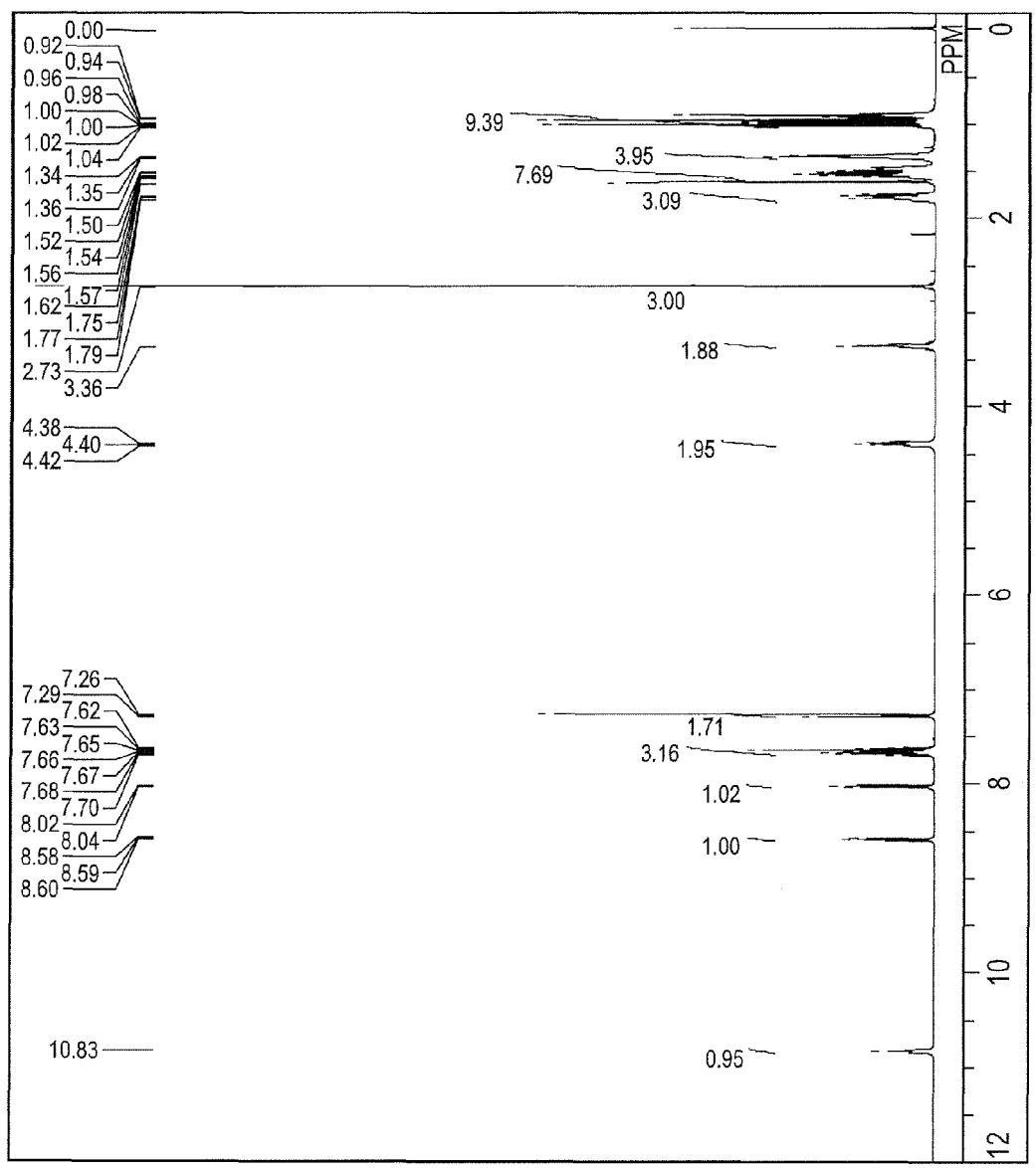

WATER-INSOLUBLE COLORING MATTER COMPOUND, INK USING THE WATER-INSOLUBLE COLORING MATTER COMPOUND, THERMAL TRANSFER RECORDING SHEET AND RESIST COMPOSITION FOR COLOR FILTER

TECHNICAL FIELD

The present invention relates to a water-insoluble coloring matter compound, and an ink containing the water-insoluble coloring matter compound used in a process for producing a coating material; an inkjet ink, a color filter, a resin molded article, and the like. The present invention further relates to a thermal transfer recording sheet using the water-insoluble coloring matter compound and a red resist composition, for a color filter.

BACKGROUND ART

Recently, color images have been increasingly utilized with color liquid crystal displays and the like, and a demand for higher image quality has been increased. Color filters are indispensable to color displays in the liquid crystal display, and an important part that governs the performance of the liquid crystal display. As a method for producing a color filter in the related art, a dyeing method, a printing method, an inkjet method, a photoresist method, and the like are known. Among these, the photoresist method is the mainstream of the production method of these days because spectral characteristics and reproductivity can be easily controlled, and high resolution enables highly fine patterning.

The photoresist method usually uses pigments as a coloring agent. Unfortunately, it is known that the pigment has a fixed particle size, and has depolarization action (a phenomenon that polarization is destroyed), reducing the contrast ratio in color display in the liquid crystal display. Moreover, a system using the pigment has difficulties in providing high transmittance of backlight, and has limitation in improving the lightness of the color filter. Further, the pigment is insoluble in organic solvents and polymers. Accordingly, a colored resist composition can be obtained as a dispersed product, but the dispersion is difficult to stabilize. Contrary to this, dyes are usually soluble in organic solvents and polymers, and do not aggregate in the colored resist composition and are stable. For this reason, in a color filter obtained from a resist composition using a dye as the coloring agent, the dye is dispersed at a molecular level and has no depolarization action. Moreover, the dye has high transmittance of the backlight. In order to provide high spectral characteristics and enable image display with high display contrast, a red color filter using a monoazo dye C.I. Acid Red 6 has been reported (see Patent Literature 1). As broadband communications are increased, development of a color filter having good spectral characteristics and high lightness and chroma to attain a high contrast ratio has been increasingly demanded in order to display highly finer images.

Meanwhile, a thermal transfer recording method is a recording method in which, a thermal transfer sheet having a coloring material layer containing a heat transferable dye and an image receiving sheet having a dye receiving layer on the surface thereof are layered on a sheet-like substrate, and recording is performed by heating the thermal transfer sheet to transfer the dye in the thermal transfer sheet onto the image receiving sheet. In the thermal transfer recording method, the thermal transfer sheet and the dye used in an ink composition for a transfer sheet are very important because these give great influences to the transfer recording speed, image quality of a recorded product, storage stability, and the like. As a dye used in such a thermal transfer recording method, an example using an anthraquinone dye has been reported (see Patent Literature 2).

However, development of a dye having high lightness and chroma and having sharpness and color reproductivity has been demanded.

CITATION LIST

Patent Literature

PTL 1: Japanese Patent Application Laid-Open No. 2003-005361

PTL 2: Japanese Patent Application Laid-Open No. H07-232481

SUMMARY OF INVENTION

Technical Problem

An object of the present invention is to solve the above problems.

Namely, an object of the present invention is to provide a dye compound having high solubility for a solvent, having high lightness and chroma, and providing a magenta chromaticity closer to a magenta chromaticity represented by an Adobe RGB color space and an ink containing the eye compound. Another object of the present invention is to provide a thermal transfer recording sheet having a good red color tone by forming a coloring material layer containing the dye compound. Further another object of the present invention is to provide a resist composition for a color filter containing the dye compound and having a good magenta color tone.

Solution to Problem

The above objects can be attained by the following invention.

The present invention relates to a water-insoluble coloring matter compound represented by the following formula (1).

The present invention also relates to an ink containing at least a water-insoluble coloring matter compound represented by the following formula (1) in a medium. The present invention further relates to a thermal transfer recording sheet and red resist composition for a color filter containing the water-insoluble coloring matter compound.

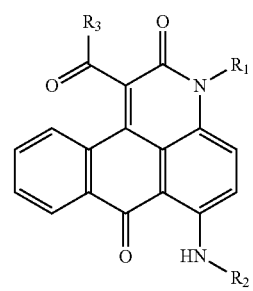

Formula (1)

wherein $R_1$ and $R_2$ represent an alkyl group, and $R_3$ represents an alkyl group, an aryl group, or an alkoxy group. The alkyl group, the aryl group and the alkoxy group regarding to $R_1$ to $R_3$ are capable of having a substituent.

Advantageous Effects of Indention

The present invention can provide a dye compound having high solubility for a solvent, having high lightness and chroma, and providing a magenta chromaticity closer to a magenta chromaticity represented by an Adobe RGB color space and an ink containing the dye compound. A thermal transfer recording sheet having a good magenta color tone can be provided by forming a coloring material layer containing the dye compound. A resist composition for a color filter having a good magenta color tone can be provided by containing the dye compound in the resist composition.

BRIEF DESCRIPTION OF DRAWING

FIGURE is a drawing illustrating a $^1$H NMR spectrum of a compound (1) represented by the formula (1) in the present invention at room, temperature and 400 MHz $CDCl_3$ in.

DESCRIPTION OF EMBODIMENTS

Hereinafter, the present invention will be described more in detail, using an embodiment. As a result of extensive research in order to solve the problems in the related art, the present inventors found out that if a water-insoluble coloring matter compound represented by the following formula (1) has high solubility for a solvent and high lightness and chroma, and an ink containing the water-insoluble coloring matter compound is provided, a magenta chromaticity closer to the magenta chromaticity represented by the Adobe RGB color space is provided, it was also found out that if the water-insoluble coloring matter compound is contained, a thermal transfer recording sheet and resist composition for a color filter having high lightness and chroma and a good magenta color tone are obtained. Thus, the present invention has been achieved.

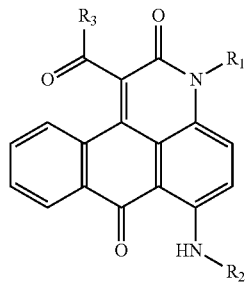

Formula (1)

wherein $R_1$ and $R_2$ represent an alkyl group, and $R_3$ represents an alkyl group, an aryl group, or an alkoxy group. And the alkyl group, the aryl group and the alkoxy group regarding to $R_1$ to $R_3$ are capable of having a substituent.

First, the water-insoluble coloring matter compound represented by the formula (1) will be described.

The water-insoluble coloring matter compound represented by the formula (1) according to the present invention has high affinity for an organic solvent. In the present invention, "water-insoluble" means that solubility in water is less than 1% in terms of mass percentage.

In the formula (1), $R_1$ and $R_2$ represent an alkyl group.

The alkyl group in $R_1$ and $R_2$ in the formula (1) is not particularly limited, and examples thereof include linear, branched, or cyclic primary to tertiary alkyl groups having 1 to 20 carbon atoms such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl, a 2-ethylhexyl group, and a cyclohexenylethyl group.

If $R_1$ is a secondary or tertiary bulky alkyl group, a cyclization step is difficult to progress, and the amount thereof to be produced is small. Accordingly, preferred are primary alkyl groups such as a methyl group, a propyl group, a butyl group, an octyl group, and a 2-ethylhexyl group. Particularly, preferred are a methyl group, an n-butyl group, and a 2-ethylhexyl group for production.

If $R_2$ is an ethyl group, an n-butyl group, a sec-butyl group, a dodecyl group, a cyclohexyl group, a methylcyclohexyl group, a 2-ethylpropyl group, a 2-ethylhexyl group, or a cyclohexenylethyl group, the compound has high lightness and chroma. Accordingly, these are preferred. Particularly, preferred are an n-butyl group and 2-ethylhexyl group.

The alkyl group in $R_1$ and $R_2$ may further have a substituent, and is not particularly limited unless the alkyl group remarkably inhibits the lightness and chroma of the compound. Examples thereof include alkoxy groups such as a methoxy group, an ethoxy group, a propoxy group, a butoxy group, and a 2-ethylhexyloxy group, monosubstituted amino groups such as a methylamino group, a propylamine group, a dimethylamino group, and a dibutylamino group, or disubstituted amino groups such as an N-ethyl-N-phenyl group, and a cyano group. Particularly, preferable are a butoxy group, a methylamino group, a dibutylamino group, an N-ethyl-N-phenyl group, and a cyano group, and the like. Among these, the butoxy group provides high lightness and chroma of the compound.

The alkyl group in $R_3$ in the formula (1) is not particularly limited, and examples thereof include linear, branched, or cyclic alkyl groups having 1 to 20 carbon atoms such as a methyl group, an ethyl group, a propyl group, a butyl group, an octyl group, a dodecyl group, a nonadeoyl group, a cyclobutyl group, a cyclopentyl group, a cyclohexyl group, a methylcyclohexyl group, or an ethylhexyl group.

The aryl group in $R_3$ is not particularly limited, and examples thereof include a phenyl group and a naphthyl group.

The alkoxy group in $R_3$ is not particularly limited, and examples thereof include a methoxy group, an ethoxy group, a propoxy group, and a butoxy group.

$R_3$ may further have a substituent, and is not particularly limited unless the alkyl group remarkably inhibits the lightness and chroma of the compound. Examples thereof include alkyl groups such as a methyl group, an ethyl group, a propyl group, and a butyl group; aryl groups such as a phenyl group; alkoxy groups such as a methoxy group, an ethoxy group, and a butoxy group; monosubstituted amino groups such as a methylamino group and a propylamine group; disubstituted amino groups such as a dimethylamino group, a dipropylamino group, and an N-ethyl-N-phenyl group; an amino group, and a cyano group.

Preferably, $R_3$ is a methyl group, a phenyl, group, a 2-methoxyphenyl group, a 4-methoxyphenyl group, or an ethoxy group. Particularly, preferred are the phenyl group, the 2-methoxyphenyl group, and the 4-methoxyphenyl group because these provide high lightness and chroma of the compound.

The compound represented by the formula (1) according to the present invention can be synthesized referring to a known method described in Japanese Patent Application Laid-Open No. 2005-320480, for example.

One embodiment of the method for producing the compound represented by the formula (1) according to the present invention will be shown, but the production method will not be limited thereto.

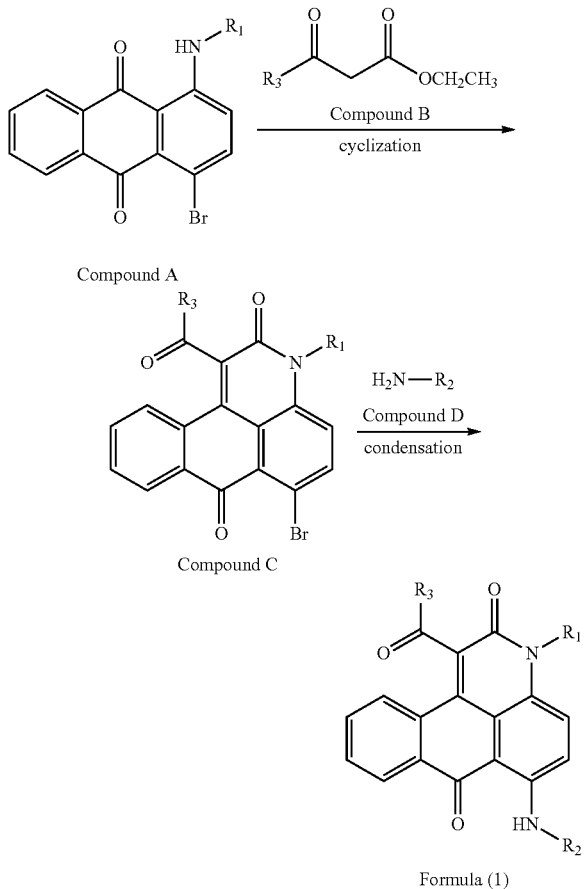

$R_1$ to $R_3$ in Compounds A to D and the formula (1) above are the same as those in $R_1$ to $R_3$ in the above-described formula (1). First, a cyclization step of cyclizing Compound A and Compound B to produce Compound C will be described.

A variety of Compound A used in the present invention is commercially available, and easily available.

The amount of Compound B to be used in this step is 0.1 to 10 times mol, preferably 0.5 to 5 times mol, and more preferably 0.8 to 5 times mol based on Compound A.

The step is preferably performed in the presence of a solvent. The solvent is not particularly limited as long as the solvent does not participate in the reaction. Examples thereof include nitrite solvents such as acetonitrile, propionitrile, and benzonitrile; aromatic solvents such as benzene, toluene, xylene, ethylbenzene, chlorobenzene, 1,2-dichlorobenzene, and mesitylene; ether solvents such as diisopropyl ether, methyl-tert-butyl ether, and tetrahydrofuran; and alcohol solvents such as butyl alcohol and diethylene glycol. Preferable are aromatic solvent such as benzene, toluene, xylene, ethylbenzene, chlorobenzene, 1,2-dichlorobenzene, mesitylene, and particularly preferable are 1,2-dichlorobenzene, mesitylene, and the like. Two or more of solvents can be mixed and used. The mixing ratio in mixing and use can be arbitrarily determined.

The amount of the above reaction solvent to be used is in the range of 0.1 to 1000 times mass, preferably 0.5 to 500 times mass, and more preferably 1.0 to 150 times mass, with respect to Compound A.

The reaction temperature in the step is in the range of −80 to 300° C., preferably −20 to 250° C., and more preferably 0 to 220° C. Usually, the reaction is completed within 48 hours.

In the step, when necessary, addition of an acid or a base accelerates the reaction. The acid, to be used is not particularly limited as long as the acid does not participate in the reaction. Examples thereof include inorganic acids such as hydrochloric acid, sulfuric acid, and phosphoric acid; organic acids such as p-toluenesulfonic acid, formic acid, acetic acid, propionic acid, and trifluoroacetic acid; strongly acid ion exchange resins such as Amberlite (Rohm and Haas Company) and AMBERLYST (Rohm and Haas Company); and inorganic acid salts such as ammonium formate and ammonium acetate. Preferable are phosphoric acid, p-toluenesulfonic acid, acetic acid, and the like.

The amount of the above acid to be used is 0.1 to 50 times mol, preferably 1 to 30 times mol, and more preferably 2 to 10 times mol, with respect to Compound A.

The base to be used in the step are specifically metal alkoxides such as potassium-tert-butoxide, sodium-tert-butoxide, sodium methoxide, and sodium ethoxide/organic salt groups such as piperidine, pyridine, 2-methylpyridine, diethylamine, triethylamine, isopropylethylamlne, potassium acetate, 1,3-diazabicyclo[5,4 0]undec-7-ene (DBU); and inorganic bases such as n-butyllithium, magnesium chloride, sodium borohydride, metal sodium, sodium hydroxide, sodium carbonate, and sodium hydrogencarbonate. Preferable are sodium methoxide, sodium ethoxide, potassium acetate, sodium carbonate, sodium hydrogencarbonate, and the like.

The amount of the base to be used is 0.1 to 15 times mol, preferably 1 to 8 times mol, and more preferably 1.4 to 5 times mol based on Compound A.

After the reaction is completed, the reaction solution is diluted with 2-propyl alcohol and hexane, and a deposited solid is filtered. Thereby, Compound C can be obtained.

Next, a condensation step will be described. The condensation step is included in a category of a known reaction classified as an Ullmann condensation reaction (Chem. Ber., 36, 2382 (1902)). Namely, Compound C and Compound D (amine compound) are condensed to obtain the compound represented by formula (1) according to the present invention. Specific examples of an amination reaction include a method shown below.

The amount of Compound D to be used in the step is 0.1 to 10 times mol, preferably 0.5 to 5 times mol, and more preferably 0.8 to 5 times mol based on Compound C.

A condensing agent to be used in the step is not particularly limited, and any condensing agent usually used in the Ullmann condensation reaction can be used. Examples thereof include copper powder and copper compounds such as cuprous chloride, cupric chloride, cuprous bromide, cupric bromide, copper iodide, copper acetate, and copper sulfate. Preferable is copper iodide.

The amount, of the condensing agent to be used is preferably 0.0005 to 0.1 mol, and more preferably 0.001 to 0.05 mol, with respect to 1 mol of Compound C.

In order to accelerate the reaction, a cocatalyst for the condensing agent can be used in the step. The cocatalyst for the condensing agent is not particularly limited as long as the condensing agent is a known cocatalyst classified as that for the Ullmann condensation reaction. For example, 2,2'-bipyridyl and 1,10-phenanthroline are preferred because these are inexpensive and easy to use.

The organic solvent used in the condensation step will be described.

The organic solvent usable in the condensation step is not particularly limited as long as the organic solvent does not participate in the reaction. For example, according to the solubility of the solute, one of methanol, ethanol, n-propanol, isopropanol, n-butanol, toluene, xylene, ethylene glycol, N-methylpyrrolidone, N,N-dimethylacetoamide, N,N-dimethylformamide, dimethyl sulfoxide, sulfolane, chlorobenzene, dichlorobenzene, trichlorobenzene, and nitrobenzene can be used, or two or more thereof can be used in combination.

The condensation step is usually performed in the range of the temperature of 0 to 220° C., and completed usually within 24 hours. The reaction temperature in the condensation step is in the range of preferably 5 to 180° C., and more preferably 10 to 120° C. At a temperature less than 0° C. the reaction progresses remarkably slowly. At a temperature more than 220° C., the compound may be decomposed. Accordingly, both cases are not preferable.

The obtained compound represented by the formula (1) is treated according to an ordinary post treatment method for the organic synthesis reaction, and recrystallization, and subjected, to refining such as reprecipitation and column chromatography. Thereby, a water-insoluble dye compound with high purity can be obtained. The water-insoluble coloring matter compound represented by the formula (1) can be identified using a $^1$H nuclear magnetic resonance spectroscope, an LC/TOF MS, or an UV/Vis spectrophotometer.

For the functional group of each compound, when necessary, persons skilled in the art can properly select and additionally perform a known protection and deprotection reaction or a reaction such as hydrolysis.

In the case where $R_1$ and $R_2$ have the same substituent, Compound E and Compound B can be cyclized to obtain the compound represented by the formula (1) according to the present invention, as shown below. The cyclization step can be performed in the same manner as in the cyclization step of cyclizing Compound A and Compound B to produce Compound C.

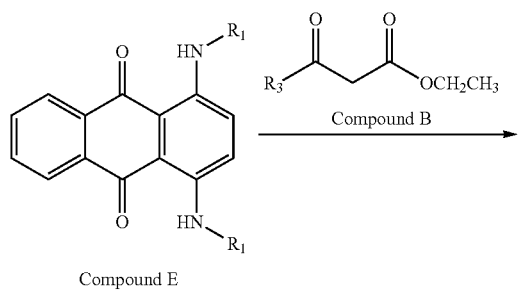

Compound E

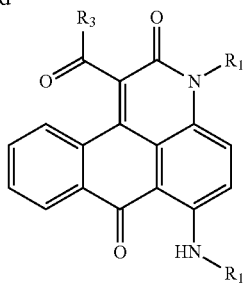

Formula (1)

In the present invention, in order to control the color tone or the like according to the purpose or application, the compound represented by the formula (1) may be used singly or in combinations of two or more. Further, two or more of known pigments and dyes can be used in combination.

As preferred specific examples of the water-insoluble coloring matter compound according to the present invention, water-insoluble coloring matter compounds (1) to (21) will be shown below, but the water-insoluble coloring matter compound according to the present invention will not be limited to the examples described below. The water-insoluble coloring matter compounds (1) to (21) each have the substituents shown in Table 1 as $R_1$, $R_2$, and $R_3$ in the following formula. "*" represents a bonding site of the substituent.

Formula (1)

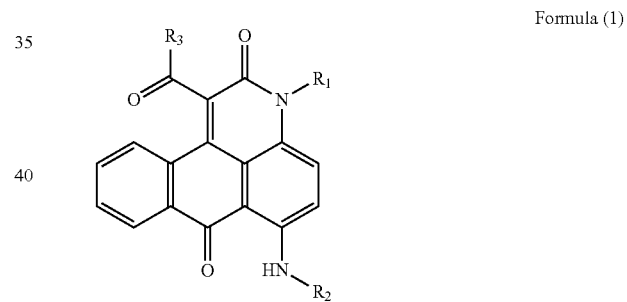

TABLE 1

| Water-insoluble compound | $R_1$ | $R_2$ | $R_3$ |
|---|---|---|---|
| (1) | CH$_3$CH$_2$CH$_2$CH$_2$—* | 2-ethylhexyl (*CH$_2$CH(CH$_2$CH$_3$)CH$_2$CH$_2$CH$_2$CH$_3$) | CH$_3$ |
| (2) | 2-ethylhexyl (*CH$_2$CH(CH$_2$CH$_3$)CH$_2$CH$_2$CH$_2$CH$_3$) | CH$_3$CH$_2$CH$_2$CH$_2$—* | CH$_3$ |
| (3) | CH$_3$ | *CH$_2$CH(CH$_3$)CH$_2$N(H)CH$_3$ | CH$_3$ |

TABLE 1-continued

| Water-insoluble compound | R₁ | R₂ | R₃ |
|---|---|---|---|
| (4) | CH₃CH₂CH₂CH₂—* | 2-ethylhexyl (*CH₂CH(C₂H₅)CH₂CH₂CH₂CH₃) | C₆H₅ |
| (5) | CH₃CH₂CH₂CH₂—* | *(CH₂)₃N((CH₂)₃CH₃)₂ (tributylamine-like) | C₆H₅ |
| (6) | CH₃CH₂CH₂CH₂—* | 2-ethylhexyl | *—C₆H₄—OCH₃ (para) |
| (7) | n-C₈H₁₇—* | CH₃CH₂CH₂CH₂—* | *-C₆H₄-OCH₃ (ortho) |
| (8) | 2-ethylhexyl | 2-ethylhexyl | C₆H₅ |
| (9) | 2-ethylhexyl | 2-ethylhexyl | *—OCH₂CH₃ |
| (10) | 2-ethylhexyl | *(CH₂)₃O(CH₂)₃CH₃ | C₆H₅ |
| (11) | 2-ethylhexyl | *(CH₂)₃OCH₂CH(C₂H₅)(CH₂)₃CH₃ | C₆H₅ |
| (12) | 2-ethylhexyl | *(CH₂)₃O(CH₂)₃CH₃ | *—OCH₂CH₃ |
| (13) | CH₃ | 2-ethylhexyl | *—C₆H₄—CH₃ (para) |
| (14) | CH₃ | 2-ethylhexyl | C₆H₅ |
| (15) | 2-ethylhexyl | *cyclohexyl | C₆H₅ |
| (16) | 2-ethylhexyl | *CH₂CH₂-(cyclohexenyl) | C₆H₅ |

TABLE 1-continued

| Water-insoluble compound | $R_1$ | $R_2$ | $R_3$ |
|---|---|---|---|
| (17) | $CH_3$ | $n\text{-}C_{12}H_{25}\text{—}*$ | $C_6H_5$ |
| (18) | 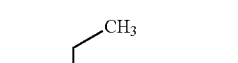 |  | $C_6H_5$ |
| (19) | 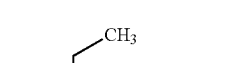 | 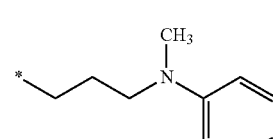 | $C_6H_5$ |
| (20) | $CH_3CH_2CH_2CH_2\text{—}*$ | $CH_3CH_2CH_2CH_2\text{—}*$ | 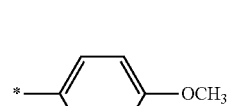 |
| (21) | $CH_3CH_2CH_2CH_2\text{—}*$ | $CH_3CH_2CH_2CH_2\text{—}*$ | $C_6H_5$ |

<Ink>

An ink according to the present invention will be Described.

The water-insoluble coloring matter compound represented by the formula (1) according to the present invention is suitable for a coloring agent for an ink because the water-insoluble coloring matter compound has high solubility for a solvent; has high lightness and chroma, and provides a magenta chromaticity closer to the magenta chromaticity represented by the Adobe RGB color space.

The ink according to the present invention is an ink containing at least a medium and at least one or more water-insoluble coloring matter compounds represented by the formula (1).

In the ink according to the present invention, components other than those above are determined according to the application of the ink according to the present invention, and an additive can be added in such a range that properties in a variety of applications of the ink are not inhibited.

The ink according to the present invention can be suitably used as an ink for inkjet, an ink for printing, a coating material, an ink for writing instruments, and the like. Among these, the ink can be particularly suitably used in the application of a resist for a color filter and as an ink for a thermal transfer recording sheet described later.

The ink according to the present invention is obtained as follows, for example.

While a medium is stirred, the water-insoluble coloring matter compound according to the present invention, and when necessary, other coloring agents, emulsifiers, resins, and the like are gradually added to the medium, and sufficiently mixed with the medium. Further, a mechanical shear force is applied with a dispersing machine to stably dissolve or finely disperse the above components. Thereby, the ink according to the present invention can be obtained.

In the present invention, the "medium" means water or an organic solvent.

In the case where an organic solvent is used as the medium for the ink according to the present invention, the kind of the organic solvent is determined according to the purpose or application of the coloring agent, and is not particularly limited. Examples thereof include alcohols such as methanol, ethanol, modified ethanol, isopropanol, n-butanol, isobutanol, tert-butanol, sec-butanol, 2-methyl-2-butanol, 3-pentanol, octanol, benzylalcohol, and cyclohexanol; glycols such as methyl cellosolve, ethyl cellosolve, diethylene glycol, and diethylene glycol monobutyl ether; ketones such as acetone, methyl ethyl ketone, and methyl isobutyl ketone; esters such as ethyl acetate, butyl acetate, ethyl propionate, and cellosolve acetate; aliphatic hydrocarbons such as nexane, octane, petroleum ether, and cyclohexane; aromatic hydrocarbons such as benzene, toluene, and xylene; halogenated hydrocarbons such, as carbon tetrachloride, trichloroethylene, and tetrabromoethane; ethers such as diethyl ether, dimethyl glycol, trioxane, and tetrahydrofuran; acetals such as methylal and diethyl acetal; organic acids such as formic acid, acetic acid, and propionic acid; and sulfur or nitrogen-containing organic compounds such as nitrobenzene, dimethylamine, monoethanolamine, pyridine, dimethylsulfoxide, and dimethylformamide.

A polymerizable monomer can also be used, as the organic solvent usable in the ink according to the present invention. The polymerizable monomer is an addition polymerizable or condensation polymerizable monomer, and is preferably an addition polymerizable monomer. Examples of such a polymerizable monomer include styrene monomers such as styrene, α-methylstyrene, α-ethylstyrene, o-methylstyrene, m-methylstyrene, p-methylstyrene, o-ethylstyrene, m-ethylstyrene, and p-ethylstyrene; acrylate monomers such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile, and acrylic acid amide; methacrylate monomers such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile, and methacrylic acid amide; olefin monomers such as ethylene, propylene, butylene, butadiene, isoprene, isobutylene, and cyclohexene; halogenated vinyl monomers such as vinyl chloride, vinylidene chloride, vinyl bromide, and vinyl iodide; vinyl ester monomers such as vinyl acetate, vinyl propionate, and vinyl benzoate; vinyl ether monomers such as vinyl methyl ether, vinyl ethyl ether, and vinyl, isobutyl ether; and vinyl ketone monomers such as vinyl methyl ketone, vinyl hexyl ketone, and methyl isopropenyl ketone. These can be used singly or when necessary in combinations of two or more.

As the coloring agent, that forms the ink according to the present invention, at least the water-insoluble coloring matter compound represented by the formula (1) is used. When necessary, other coloring agents can be used in combination unless the other coloring agent inhibits the solubility or dispersibility of the water-insoluble coloring matter compound for the medium.

Examples of the coloring agent usable in combination include condensation azo compounds, azo metal complexes, diketopyrrolepyrrole compounds, anthraquinone compounds, xanthene compounds, quinacridone compounds, naphthol compounds, benzimidazolone compounds, thioindigo compounds, perylene compounds, methine compounds, allylamide compounds, and basic dye lake compounds. Specifically, examples thereof include, but not limited to, C.I. Pigment Oranges 1, 5, 13, 15, 16, 34, 36, 38, 62, 64, 67, 72, and 74; C.I. Pigment Reds 2, 3, 4, 5, 6, 7, 12, 16, 17, 23, 31, 32, 41, 48, 48:1, 48:2, 48:3, 48:4, 53:1, 57:1, 81:1, 112, 122, 123, 130, 144, 146, 149, 150, 166, 168, 169, 170, 176, 177, 178, 179, 181, 184, 185, 187, 190, 194, 202, 206, 208, 209, 210, 220, 221, 224, 238, 242, 245, 253, 254, 255, 258, 266, 269, and 282; and C.I. Pigment Violets 13, 19, 25, 32, and 50; and various coloring agents classified as a derivative thereof.

The amount of the above coloring agent that forms the ink according to the present invention is 1.0 to 30.0 parts by mass, preferably 2.0 to 20.0 parts by mass, and more preferably 3.0 to 15.0 parts by mass, based on 100.0 parts by mass of the medium. At an amount in these ranges, a sufficient coloring ability is obtained, and the coloring agent has high dispersibility.

In the case where water is used as the medium, for the ink according to the present invention, when necessary, an emuisifier can be added to provide high disperse stability of the above coloring agent. The emuisifier that can be added is not particularly limited, and examples thereof include cationic surfactants, anionic surfactants, and nonionic surfactants.

Examples of the cationic surfactants as the above emulsifier include dodecylammonium chloride, dodecylammonium bromide, dodecyltrimethylammonium bromide, dodecylpyridinium chloride, dodecylpyridinium bromide, and hexadecyltrimethylammonium bromide.

Examples of the anionic surfactants as the above emulsifier include fatty acid soaps such as sodium stearate, and sodium dodecanoate, sodium dodecyl sulfate, sodium dodecylhenzene sulfate, and sodium laurylsulfate.

Examples of the nonionic surfactants as the above emulsifier include dodecyl polyoxyethylene ether, hexadecyl polyoxyethylene ether, nonylphenyl polyoxyethylene ether, lauryl polyoxyethylene ether, sorbitan, monooleate polyoxyethylene ether, and monodecanoyl sucrose.

Further, a resin can be added to the ink according to the present invention. The kind of the resin that can be added to the ink according to the present invention is determined according to the purpose or application, and is not particularly limited. Examples thereof include polystyrene resins, styrene copolymers, polyacrylic acid resins, polymethacrylic acid resins, polyacrylate resins, polymethacrylate resins, acrylic acid copolymers, methacrylic acid copolymers, polyester resins, polyvinyl ether resins, polyvinyl methyl ether resins, polyvinyl alcohol resins, polyvinylbutyral resins, polyurethane resins, and polypeptide resins. These resins can be used singly or when necessary in combinations of two or more.

The dispersing machine used in the step is not particularly limited. For example, media dispersing machines such as rotary shear type homogenizers, ball mills, sand mills, and Attritors, and high pressure counter collision dispersing machines can preferably be used.

As above, the ink according to the present invention has a vivid red to magenta color tone because the ink includes the water-insoluble coloring matter compound according to the present invention having high solubility for a solvent and high lightness and chroma and providing a magenta chromaticity closer to the magenta chromaticity represented by the Adobe RGB color space.

<Thermal Transfer Recording Sheet>

Next, a thermal transfer recording sheet according to the present invention will be described.

The water-insoluble coloring matter compound according to the present invention can be suitably used in a thermal transfer recording sheet because the water-insoluble coloring matter compound has high solubility for a solvent and high lightness and chroma, and provides a magenta chromaticity closer to the magenta chromaticity represented by the Adobe RGB color space.

The thermal transfer recording sheet according to the present invention has a substrate and a coloring material layer formed by applying at least the water-insoluble coloring matter compound according to the present invention onto the substrate to form a film.

The thermal transfer recording sheet according to the present invention is obtained as follows, for example. A coloring agent containing at least the water-insoluble coloring matter compound represented by the formula (1), a binder resin, and when necessary, a surfactant, wax, and the like are gradually added to a medium while the medium is stirred, and are sufficiently mixed with the medium. Further, a mechanical shear force is applied with a dispersing machine to stably dissolve the above composition or disperse the composition into fine particles. Thereby, the ink according to the present invention is prepared. Next, the ink is applied onto a base film as the substrate, and dried. Thereby, the thermal transfer recording sheet according to the present invention can be produced. The present, invention will not be limited to the thermal transfer recording sheet produced by the method.

Examples of the binder resin usable in the thermal transfer recording sheet, according to the present invention include various resins. Among these, preferred are water-soluble resins such as cellulose resins, polyacrylic acid resins, starch resins, and epoxy resins; and organic-solvent-soluble resins such as polyacrylate resins, polymethacrylate resins, polystyrene resins, polycarbonate resins, polyethersulfone resins, polyvinyl butyral resins, ethyl cellulose resins, acetyl cellulose resins, polyester resins, AS resins, and phenoxy resins. These resins can be used singly or when necessary in combinations of two or more.

The same medium used for the above ink can also be used as the medium usable in the above production method. Specifically, examples of the medium include water or organic solvents. As the organic solvent, preferably used are, for example, alcohols such as methanol, ethanol, isopropanol, and isobutanol; cellosolves such as methyl cellosolve and ethyl cellosolve; aromatic hydrocarbons such as toluene, xylene, and chlorobenzene; esters such as ethyl acetate and butyl acetate; ketones such as acetone, methyl ethyl ketone, methyl isobutyl ketone, and cyclohexanone; halogenated hydrocarbons such as methylene chloride, chloroform, and trichloroethylene; ethers such as tetrahydrofuran and dioxane; N,N-dimethylformamide, and N-methylpyrrolidone. The above organic solvents can be used singly or when necessary in combinations of two or more.

In the thermal transfer recording sheet according to the present invention, if at least the water-insoluble coloring matter compound represented by the above formula (1) is used as the coloring agent, a thermal transfer recording sheet having high lightness and chroma and a good color tone can be obtained. Further, in order to obtain desired spectral characteristics, other dyes can be used in combination for color toning. The dye usable in combination is not limited unless the dye gives a great influence to the lightness, chroma, and light fastness of the thermal transfer recording sheet according to the present invention. Examples of the dye include C.I. Solvent Reds 8, 27, 35, 36, 37, 38, 39, 40, 49, 58, 60, 65, 69, 81, 83:1, 86, 89, 91, 92, 97, 99, 100, 109, 118, 119, 122, 127, and 218; C.I. Disperse Reds 1, 59, 60, 73, 135, 146, and 167; and C.I. Disperse Violet 26.

The ratio of the above binder resin to the above coloring agent to be used (binder resin: coloring agent) is preferably in the range of 1:2 to 2:1 in terms of mass ratio from the viewpoint of transfer properties.

A surfactant can be added to the thermal transfer recording sheet according to the present invention in order to provide sufficient lubrication while heating a thermal head (during printing). Examples of the surfactant that can be added include cationic surfactants, anionic surfactants, and nonionic surfactants.

Examples of the cationic surfactant include dodecylammonium chloride, dodecylammonium bromide, dodecyltrimethylammonium bromide, dodecylpyridinium chloride, dodecylpyridinium bromide, and hexadecyltrimethylammonium bromide.

Examples of the anionic surfactant include fatty acid soaps such as sodium, stearate and sodium dodecanoate, sodium dodecyl sulfate, sodium dodecylbenzene sulfate, and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

A wax can be added to the thermal transfer recording sheet according to the present, invention in order to provide sufficient lubrication while not heating the thermal head. Examples of the wax that can be added include, but not limited to, polyethylene waxes, paraffin waxes, and fatty acid, ester waxes.

Other than the above additives, when necessary, an ultraviolet absorbing agent, a preservative agent, an antioxidant, an antistatic agent, a viscosity adjuster, and the like may be added, to the thermal transfer recording sheet according to the present invention.

The base film as the substrate in the thermal transfer recording sheet according to the present invention is not particularly limited. For example, preferable are tissue papers such as capacitor paper and glassine paper, and plastic films formed with polyester, polycarbonate, polyamide, polyimide, and polyaramid because of high heat resistance, and more preferable are polyethylene terephthalate films from the viewpoint of mechanical strength, solvent resistance, and economy and the like. The thickness of the substrate is preferably 3 to 50 μm from the viewpoint, of the transfer properties.

In the thermal transfer recording sheet according to the present invention, in order to improve heat resistance and travelling properties of the thermal head, a thermal resin layer formed with, a lubricant, a highly lubricant heat-resistant fine particle, and a binder is preferably provided on the surface opposite to the coloring material layer of the substrate. Examples of the lubricant include, but not limited to, amino-modified silicone compounds and carboxy-modified silicone compounds. Examples of the heat resistant fine particle include, but not limited to, fine particles such as silica. Examples of the binder include, but not limited to, acrylic resins.

The dispersing machine used in the above dispersing step is not particularly limited. For example, media dispersing machines such as rotary shear type homogenizers, ball mills, sand mills, and Attritors, and high pressure counter collision dispersing machines can be preferably used.

The method for applying the ink to the above base film is not particularly limited, and examples thereof include methods using a bar coater, a gravure coater, a reverse roll coater, a rod coater, an air doctor coater, or the like. From the viewpoint of the transfer properties, the application amount of the above ink composition is preferably such that the thickness of the coloring material layer after drying is in the range of 0.1 to 5 μm.

The heating unit for heating the thermal transfer recording sheet according to the present invention is not particularly limited. For example, not only a standard method using a thermal head but also a method using infrared rays or laser light can be used. Alternatively, an electrical heating film that generates heat by electrically conducting the base film can be used as an electrically conductive dye transfer sheet.

As above, the thermal transfer recording sheet according to the present invention includes the water-insoluble coloring matter compound according to the present invention having a vivid red color tone, and can provide a thermal transfer recording sheet having a vivid red color tone.

<Resist Composition for Color Filter>

Next, a resist composition for a color filter according to the present invention will be described.

The ink according to the present invention can be suitably used for a red resist composition for a color filter because the ink has high solubility for a solvent and high lightness and chroma, and provides a magenta chromaticity closer to the magenta chromaticity represented by the Adobe RGB color space.

The resist composition for a color filter according to the present invention includes at least a binder resin, a medium, and the water-insoluble coloring matter compound, according to the present invention.

The resist composition for a color filter according to the present invention is obtained as follows, for example. While a medium, is stirred, an ink containing the water-insoluble coloring matter compound according to the present invention, a binder resin, send when necessary, a polymerizable monomer, a polymerisation initiator, a photoacid generator, and the like are gradually added to the medium, and sufficiently mixed with the medium. Further, a mechanical shear force is applied, with a dispersing machine to stably dissolve or finely disperse the composition. Thereby, the resist composition for a color filter according to the present, invention can be obtained, here, the ink is added to provide the water-insoluble coloring matter compound in the resist composition. But the water-insoluble coloring matter compound may be added on other forms, or may be directly dispersed in the medium.

The binder resin, usable for the resist composition for a color filter according to the present invention is not particularly limited as long as one of a light irradiated portion or a light shielding portion in a light exposing step in formation of pixels can be dissolved in an organic solvent, an alkaline agueous solution, water, a commercially available developing solution, or the like. Among these, preferred are those having a composition that can be developed with water or an alkaline aqueous solution, from the viewpoint of workability, waste treatment, and the like.

As the above binder resin, known are binder resins obtained, by usually copolymerizing a hydrophilic polymerizabie monomer such as acrylic acid, methacrylic acid, N-(2-hydroxyethyl) acrylamide, N-vinylpyrrolidone, and a polymerizable monomer having an ammonium salt with a lipophilic polymerizable monomer such as acrylic acid esters, methacrylic acid, esters, vinyl acetate, styrene, and N-vinylcarbazole in a proper mixing ratio by a known method. If these binder resins are used in combination with a radically polymerizable monomer having an ethylenically unsaturated, group, a cationically polymerizabie monomer having an oxirane ring or an oxetane ring, a radical generator, an acid generator, or a base generator, these binders can be used for a negative type resist, namely, a resist, of a type in which the solubility in the developing solution is reduced by light exposure, and only the light shielding portion is removed by development.

Alternatively, for example, a resin having a quinone diazide group that cleaves by light to generate a carboxylic acid group, or a combination of a binder resin having a group that cleaves by an acid such as tert-butylcarbonic acid ester of polyhydroxystyrene and tetrahydropyranyl ether with an acid generator that generates an acid by light exposure can be used. The binder resin of this kind can be used for a positive type resist, namely, a resist of such a type that the solubility in the developing solution is improved by light exposure, and only the light exposed portion is removed by development.

In the case where the resist composition for a color filter according to the present invention is the above negative resist composition, the resist composition includes a photopolymerizable monomer having one or more ethylenically unsaturated double bonds as a polymerizable monomer that is addition-polymerized by light exposure. Examples of the photopolymerizable monomer include compounds having at least one addition-polymerizable ethylenically unsaturated group in the molecule and having a boiling point at normal pressure of not less than 100° C. Examples of the compounds can include monofunctional acrylates such as polyethylene glycol monoacrylate, polyethylene glycol monomethacrylate, polypropylene glycol monoacrylate, polypropylene glycol monomethacrylate, phenoxyethyl acrylate, and phenoxyethyl methacrylate; polyfunctional acrylates or methacrylates such as polyethylene glycol diacrylate, polyethylene glycol dimethacrylate, polypropylene glycol diacrylate, polypropylene glycol dimethacrylate, trimethylolethane triacrylate, trimethylolethane trimethacrylate, trimethylolpropane triacrylate, trimethylolpropane trimethacrylate, trimethylolpropane diacrylate, trimethylolpropane dimethacrylate, neopentyl glycol diacrylate, neopentyl glycol dimethacrylate, pentaerythritol tetraacrylate, pentaerythritol, tetramethacrylate, pentaerythritol triacrylate, pentaerythritol trimethacrylate, dipentaerythritol hexaaerylate dipentaerythritol hexamethacrylate, dipentaerythritol pentaacrylate, dipentaerythritol pentamethacrylate, hexanediol diacrylate, hexanediol dimethacrylate, trimethylolpropane tri(acryloyloxypropyl) ether, tri(acryloyloxyethyl)isocyanurate, tri(acryloyloxyethyl)cyanurate, glycerol triacrylate, and glycerol trimethacrylate; or polyfunctional acrylates and polyfunctional methacrylates such as those obtained by adding ethylene oxide or propylene oxide to a polyfunctional alcohol such as trimethylolpropane and glycerol followed by acrylation or methacrylation. Examples thereof further include urethane acrylates, polyester acrylates, and polyfunctional epoxy acrylates and epoxy methacrylates that are reaction products of an epoxy resin with an acrylic acid or a methacrylic acid. Among these, preferably usable are trimethylolpropane triacrylate, trimethylolpropane trimethacrylate, pentaerythritol tetraacrylate, pentaerythritol tetramethacrylate, dipentaerythritol hexaacrylate, dipentaerythritol hexamethacrylate, dipentaerythritol pentaacrylate, dipentaerythritol pentamethacrylate, and the like.

The above photopolymerizable monomers may be singly or when necessary in combinations of two or more.

The content of the above photopolymerizable monomer is preferably 5 to 50% by mass, and more preferably 10 to 40% by mass, based on the mass of the resist composition according to the present invention (the total solid content). At a content thereof less than 5% by mass, sensitivity to light exposure and strength of the pixel may be reduced. At a content more than 50% by mass, the resist composition may have excessive tackiness. Accordingly, both cases are not preferable.

In the case where the resist composition for a color filter according to the present invention is the above negative resist composition, the resist composition includes a photopolymerization initiator. Examples of the photopolymerization initiator include vicinal polyketoaldonyl compounds, α-carbonyl compounds, acyloin ether, polynuclear quinone compounds, a combination of triallylimidazole dimer/p-aminophenylketone, and trioxadiazole compounds. Preferably, examples thereof include 2-benzyl-2-dimethylamino-1-(4-morpholinophenyl) butanone (trade name: IRGACURE 369, made by BASF SE). The above photopolymerization initiator is not essential if an electron beam is used in formation of pixels using a coloring resist according to the present invention.

In the case where the resist composition for a color filter according to the present invention is the above positive resist composition, a photoacid generator can be added when necessary. Known photoacid generators such as salts of an onium ion such as sulfonium, iodonium, selenium, ammonium, and phosphonium and an anion can be used, but the photoacid generator will not be limited to these.

Examples of the above sulfonium ion include triphenylsulfonium, tri-p-tolylsulfonium, tri-o-tolylsulfonium, tris(4-methoxyphenyl)sulfonium, 1-naphthyldiphenylsulfonium, diphenylphenacylsulfonium, phenylmethylbenzylsulfonium, 4-hydroxyphenylmethylbenzylsulfonium, dimethylphenacylsulfonium, and phenacyl tetrahydrothiophenium.

Examples of the above iodonium ion include diphenyliodonium, di-p-tolyliodonium, bis(4-dodecylphenyl)iodonium, bis(4-methoxyphenyl)iodonium, and (4-octyloxyphenyl)phenyliodonium.

Examples of the above selenium ion include triarylseleniums (triphenylselenium, tri-p-tolylselenium, tri-o-tolylselenium, tris(4-methoxyphenyl)selenium, 1-naphthyldiphenylselenium, tris(4-fluorophenyl)selenium, tri-1-naphthylselenium, and tri-2-naphthylselenium).

Examples of the above ammoniumion include tetraalkylammoniums (tetramethylammonium, ethyltrimethylammonium, diethyldimethylammonium, triethylmethylammonium, tetraethylammonium, trimethyl-n-propylammonium, trimethylisopropylamnionium, trimethyl-n-butylammonium, and trimethylisobutylammonium).

Examples of the above phosphonium ion include tetraphenylphosphonium, tetra-p-tolylphosphonium, tetrakis(2-methoxyphenyl)phosphonium, triphenylbenzylphosphonium, triphenylphenacylphosphonium, triphenylmethylphosphonium, triethylbenzylphosphonium, and tetraethylphosphonium.

As the above anion, for example, perhalogen acid ions such as $ClO_4^-$ and $BrO_4^-$; halogenated sulfonic acid ions such as $FSO_3^-$ and $ClSC_3^-$; sulfuric acid ions such as $CH_3SO_4^-$, $CF_3SO_4^-$, and $HSO_4^-$; carbonate ions such as $HCO_3^-$ and $CH_3CO_3^-$; aluminate ions such as $AlCl_4^-$ and $AlF_4^-$; hexafluorobismuth acid ions; carboxylic acid ions such as $CH_3COO^-$, $CF_3COO^-$, $C_6H_5COO^-$, $CH_3C_6H_4COO^-$, $C_6F_5COO^-$, and $CF_3C_6H_4COO^-$; arylboric acid ions such as $B(C_6H_5)_4^-$ and $CH_3CH_2CH_2CH_2B(C_6H_5)_3^-$; and thiocyan acid ions; and nitric acid ions can be used, but the anion will not be limited to these.

In the resist composition for a color filter according to the present invention, examples of a medium for dissolving or dispersing the ink, the binder resin, and the photopolymerizable monomer, photopolymerization initiator, photo-acid generator added when necessary include water or various organic solvents. Examples of the organic solvents include cyclohexanone, ethyl cellosolve acetate, butyl cellosolve acetate, 1-methoxy-2-propylacetate, diethylene glycol dimethyl ether, ethylbenzene, 1,2,4-trichlorobenzene, ethylene glycol diethyl ether, xylene, ethyl cellosolve, methyl-n-amylketone, propylene glycol monomethyl ether, toluene, methyl ethyl ketone, ethyl, acetate, methanol, ethanol, isopropanol, butanol, methyl isobutyl ketone, and petroleum solvents. These can be used singly or in combinations of two or more. The medium for the resist composition for a color filter according to the present invention may be the same medium as that used for the above ink unless the medium inhibits dispersibility of the coloring agent in the above ink.

In the color filter in which two or more pixels having different spectral characteristics are arranged adjacent to each other, the resist composition including the ink according to the present invention is used for the pixel that forms at least one color among a plurality of colors of the pixels (for example, red, green, and blue). Thereby, a filter having high lightness and chroma and a good color tone can be obtained. Further, in order to obtain desired spectral characteristics, other dyes can be used in combination for toning the color. The dye usable in combination is not particularly limited, and examples thereof include C.I. Solvent Blues 14, 24, 25, 26, 34, 37, 38, 39, 42, 43, 44, 45, 48, 52, 53, 55, 59, 67, and 70; C.I. Solvent Reds 8, 27, 35, 36, 37, 38, 39, 40, 49, 58, 60, 65, 69, 81, 83:1, 86, 89, 91, 92, 97, 99, 100, 109, 118, 119, 122, 127, and 218; and C.I. Solvent Yellows 1, 2, 3, 13, 14, 19, 21, 22, 29, 36, 37, 38, 39, 40, 42, 43, 44, 45, 47, 62, 63, 71, 76, 79, 81, 82, 83:1, 85, 86, 88, and 151.

Other than the above additives, when necessary, an ultraviolet absorbing agent, or a silane coupling agent for improving adhesion to the glass substrate in production of the filter may be added to the resist composition for a color filter according to the present invention.

The dispersing machine used in the step is not particularly limited. For example, media dispersing machines such as rotary shear type homogenizers, ball mills, sand mills, and Attritors, and high pressure counter collision dispersing machines can be preferably used.

As above, the resist composition for a color filter according to the present invention includes the water-insoluble coloring matter compound according to the present invention having a vivid magenta color tone. Accordingly, the resist composition is suitably used as the magenta resist composition, and can suitably provide a color filter having a vivid magenta color tone. Moreover, a dye compound of other colors can be used in combination to produce a resist composition for a color filter other than magenta.

EXAMPLES

Hereinafter the present invention will be described more in detail using Examples and Comparative Example, but the present invention will not be limited to these Examples. Herein, "parts" and "%" are based on mass unless otherwise specified.

The obtained reaction product was identified, by a plurality of analysis methods using apparatuses shown below. Namely, the analysis apparatuses used were a $^1H$ nuclear magnetic resonance spectroscope (ECA-400, made by JEOL, Ltd.), an LC/TOF MS (LC/MSD TOP, made by Agilent Technologies, Inc.), an UV/Vis spectrophotometer (UV-36000 spectrophotometer, made by SHIMADZU Corporation). The ionization method in the LC/TOF MS used was an electrospray ionization method (ESI).

Production of Compound Represented by Formula (1)

The compound represented by the formula (1) according to the present invention can be synthesized by a known method. According to the method described below, the compound represented by the formula (1) according to the present invention was produced.

Production Example 1

Production Example of Compound (1)

10.4 g (80 mmol) of ethyl acetoacetate and 0.7 g (6.4 mmol) of sodium carbonate were suspended in 40 ml, of 1,2-dichlorobenzene of 14.3 g (40 mmol) of 4-bromo-1-butylaminoanthraquinone, and the suspension was stirred at 175° C. for 24 hours. After the reaction was completed, the reaction solution was cooled to room temperature, and diluted with 50 mL of 2-propylalcohol and 50 ml of hexane. The solid was filtered, and washed with 100 mL of 2-propylalcohol to obtain 8 g of an intermediate product (1) corresponding to Compound C. 3.6 mL of 2-ethylhexylamine, 292 mg of copper(I) iodide, and 4.7 g of sodium carbonate were added to a solution of 75 mL of dimethylformamide of 7 g (14.6 mmol) of the intermediate product (1), and the reaction was conducted at 100° C. for 2 hours. After the reaction was completed, the reaction solution was cooled, diluted with 200 mL of ethyl acetate, and filtered. Column, chromatography refining (toluene/THF) was performed, to obtain 5.7 g (yield of 30%) of the compound (1). The $^1H$ NMR spectrum at room temperature and 400 MHz in $CDCl_3$ of the compound (1) is illustrated in FIGURE.

The solubility in water of the compound at room temperature and that, at 60° C. were measured, and it was found that both were less than 1% in terms of mass percentage.

<Result of Analysis of Compound (1)>

[1] $^1H$ NMR (400 MHz, $CDCl_3$, Room temperature): δ [ppm]=0.97 (tt, 9H, J=20.6, 7.25 Hz), 1.32 (td, 4H, J=15.0, 14.2 Hz), 1.62-4.46 (m, 6H), 1.74-1.63 (m, 3H), 2.73 (s, 3H), 3.36 (m, 2H), 4.40 (t, 2H, J=7.79 Hz), 7.28 (d, 2H, J=9.62 Hz), 7.61-7.70 (m, 3 Hz), 8.03 (d, 1H, J=7.79 Hz), 8.59 (dd, 1H, J=7.79, 1.83 Hz), 10.8 (s, 1H)

[2] Mass spectrometry (ESI-TOF); m/z=473.2898 $(M+H)^+$

[3] UV/Vis spectral analysis: λmax=556 nm

Production Example 2

Production Example of Compound (4)

The same operation as that in Production Example 1 was performed except that ethyl acetoacetate in Production Example 1 was replaced by ethyl benzoylacetate. Thus, 6.6 g (yield of 32%) of a compound (4) was obtained.

The solubility in water of the compound at room temperature and that at 60° C. were measured, and it was found that both were less than 1% in terms of mass percentage.

<Result of Analysis of Compound (4)>

[1] $^1$H NMR (400 MHz, CDCl$_3$, Room temperature): δ [ppm]=0.96 (dt, 9H, J=25.0, 7.21 Hz), 1.36-1.39 (m, 4H), 1.45-1.61 (m, 6H), 1.79 (t, 3H, J=6.18 Hz), 3.37-3.41 (m, 2H), 4.39 (s, 2H), 7.32-7.47 (m, 4H), 4.75 (tt, 2 Hz, J=7.56, 2.44 Hz), 7.72 (d, 1H, J=10.1 Hz), 7.97-8.03 (m, 3H), 8.55 (dd, 1H, J=7.79, 1.37 Hz), 10.9 (s, 1H)

[2] Mass spectrometry (ESI-TOF): m/z=535.3001 (M+H)$^+$

[3] UV/Vis spectral analysis: λmax=558 nm

Production Example 3

Production Example of Compound (5)

The same operation as that in Production Example 1 was performed except that ethyl acetoacetate in Production Example 1 was replaced by ethyl 4-methoxybenzoylacetate. Thus, 5.4 g (yield of 24%) of a compound (6) was obtained.

The solubility in water of the compound at room temperature and that at 60° C. were measured, and it was found that both were less than 1% in terms of mass percentage.

<Result of Analysis of Compound (6)>

[1] $^1$H NMR (400 MHz, CDCl$_3$, Room temperature): δ [ppm]=0.90 (dt, 9H, J=24.9, 7.21 Hz), 1.31 (t, 4H, J=3.66 Hz), 1.44 (dd, 4H, J=14.9, 7.56 Hz), 1.52 (dd, 2H, J=16.5, 7.33 Hz), 1.73 (t, 3H, J=6.18 Hz), 3.78 (s, 1H), 4.33 (d, 2H, 43.1 Hz), 6.86 (d, 2H, J=9.16 Hz), 7.24 (t, 1H, J=11.5 Hz), 7.34 (t, 1H, J=7.79 Hz), 7.51 (t, 1H, J=7.56 Hz), 7.65 (d, 1H, J=9.62 Hz), 7.92 (d, 2H, J=8.70 Hz), 8.01 (d, 1H, J=8.24 Hz), 10.8 (s, 1H)

[2] Mass spectrometry (ESI-TOF): m/z=565.3048 (M+H)$^+$

[3] UV/Vis spectral analysis: λmax=557 nm

Production Example 4

Production Example of Compound (8)

The same operation as that in Production Example 1 was performed except that 4-bromo-1-butylaminoanthraquinone in Production Example 1 was replaced by 4-bromo-1-(2-ethylhexyl)aminoanthraquinone, and ethyl acetoacetate was replaced by ethyl benzoylacetate. Thus, 3.9 g (yield of 17%) of a compound (8) was obtained.

The solubility for water of the compound at room temperature and that at 60° C. were measured, and it was found that both were less than 1% in terms of mass percentage.

<Result of Analysis of Compound (8)>

[1] $^1$H NMR (400 MHz, CDCl$_3$, Room temperature): δ [ppm]=0.88 (dq, 12H, J=41.1, 10.1 Hz), 1.19-1.34 (m, 12H), 1.49 (dt, 4H, J=22.3, 8.24 Hz), 1.74 (t, 1H, J=6.18 Hz), 1.91 (s, 1H), 3.32 (t, 2H, J=4.12 Hz), 4.34 (br, 2H), 7.24 (t, 1H, J=10.3 Hz), 7.32-7.42 (m, 3H), 7.50-7.54 (m, 2H), 7.67 (d, 1H, J=9.62 Hz), 7.95 (dd, 3H, J=15.1, 7.79 Hz), 8.50 (d, 1H, J=6.87 Hz) 10.8 (3, 1H)

[2] Mass spectrometry (ESI-TOF): m/z=591.3567 (M+H)$^+$

[3] UV/Vis spectral analysis: λmax=559 nm

Production Example 5

Production Example of Compound (9)

The same operation as that in Production Example 1 was performed except that 4-bromo-1-butylaminoanthraquinone in Production. Example 1 was replaced by 4-bromo-1-(2-ethylhexyl)aminoanthraquinone, and ethyl acetoacetate was replaced by diethyl malonate. Thus, 4.6 g (yield of 21%) of a compound (9) was obtained. The solubility in water of the compound at room temperature and that at 60° C. were measured, and it was found that both were less than 1% in terms of mass percentage.

<Result of Analysis of Compound (9)>

[1] $^1$H NMR (400 MHz, CDCl$_3$, Room temperature): δ [ppm]=0.90 (tt, 12H, J=19.0, 7.02 Hz), 1.23-1.55 (m, 19H), 1.74 (t, 1H, J=6.18 Hz), 1.93 (d, 1H, J=3.66 Hz), 3.32 (s, 2H), 4.38 (d, 2H, J=23.8 z), 4.54 (q, 2H, J=6.72 Hz), 7.23 (d, 1H, J=9.62 Hz), 7.64 (dq, 3 Hz, J=16.3, 4.73 Hz), 8.19 (d, 1H, J=7.79 Hz), 8.55 (t, 1H, J=4.58 Hz), 10.8 (s, 1H)

[2] Mass spectrometry (ESI-TOF): m/z=550.3497 (M+K)$^+$

[3] UV/Vis spectral analysis: λmax=559 nm

Production Example 6

Production Example of Compound (10)

The same operation as that in Production Example 1 was performed except that 4-bromo-1-butylaminoanthraquinone in Production Example 1 was replaced by 4-bromo-1-(2-ethylhexyl)aminoanthraquinone, ethyl acetoacetate was replaced by ethyl benzoylacetate, ethyl acetoacetate was replaced by diethyl malonate, and 2-ethylhexylamine was replaced by 3-butoxy-propylamine. Thus, 5.2 g (yield of 22%) of a compound (10) was obtained. The solubility in water of the compound at room temperature and that at 60 C. were measured, and it was found that both were less than 1% in terms of mass percentage.

<Result of Analysis of Compound (10)>

[1] $^1$H NMR (400 MHz, CDCl$_3$, Room temperature): δ [ppm]=0.84-0.94 (m, 9H), 1.24-1.42 (m, 10H), 1.58 (td, 2H, J=14.3, 7.48 Hz), 1.93 (s, 1H), 2.02-2.08 (m, 2H), 3.45 (t, 2H, J=6.64 Hz), 3.58 (q, 4H, J=6.72 Hz), 4.37 (br, 2H), 7.32-7.45 (m, 4H), 7.53-7.57 (m, 2 Hz), 7.70 (d, 1H, J=9.62 Hz), 7.98 (dd, 3H, J=13.3, 7.79 Hz), 8.51 (d, 1H, J=6.41 Hz), 10.8 (s, 1H) [2] Mass spectrometry (ESI-TOF): m/z=593.3361 (M+H)$^+$ [3]

UV/Vis spectral analysis: λmax=555 nm.

Production Example 7

Production Example of Compound (14)

The same operation as that in Production Example 1 was performed except that 4-bromo-1-butylaminoanthraquinone in Production Example 1 was replaced, by 4-bromo-1-methylaminoanthraquinone, and ethyl acetoacetate was replaced by ethyl benzoylacetate. Thus, 5.0 g (yield of 25%) of a compound (14) was obtained. The solubility for water of the compound at room temperature and that at 60° C. were measured, and it was found that both were less than 1% in terms of mass percentage.

<Result of Analysis of Compound (14)>

[1] $^1$H NMR (400 MHz, CDCl$_3$, Room temperature): δ [ppm]=0.91 (t, 3H, J=6.87 Hz), 0.97 (t, 3H, J=7.56 Hz), 1.34 (t, 4H, J=3.66 Hz), 1.52 (m, 4H), 1.77 (t, 1H, 6.18 Hz), 3.35 (t, 2H, J=4.35 Hz), 3.84 (s, 3H), 7.30 (d, 1H, J=9.62 Hz), 7.40 (td, 3H, J=15.2, 7.94 Hz), 7.55 (t, 2H, J=7.10 Hz), 7.72 (d, 1H, J=9.62 Hz), 7.96 (dd, 3H, J=10.7, 8.70 Hz), 8.53 (d, 1H, J=7.79 Hz), 10.8 (s, 1H)

[2] Mass spectrometry (ESI-TOF): m/z=493.2504 (M+H)$^+$

[3] UV/Vis spectral analysis: λmax=560 nm

Production Example 8

Production Example of Compound (15)

The same operation as that in Production Example 1 was performed except that ethyl acetoacetate in Production Example 1 was replaced by ethyl benzoylacetate, and 2-ethylhexylamine was replaced by cyclohexylamine. Thus, 6.8 g (yield of 30%) of compound (15) was obtained. The solubility in water of the compound at room temperature and that at 60° C. were measured, and it was found that both were less than 1% in terms of mass percentage.

<Result of Analysis of Compound (15)>

[1] $^1$H NMR (400 MHz, CDCl$_3$, Room temperature): δ [ppm]=0.87 (t, 6H, J=11.0 Hz), 1.24-1.66 (m, 14H), 1.88 (s, 3H), 2.10 (s, 2H), 3.68 (s, 1H), 4.37 (s, 1H), 7.36 (dq, 4H, J=32.9, 8.93 Hz), 7.55 (dd, 2H, J=10.3, 4.81 Hz), 7.68 (d, 1H, J=9.62 Hz), 7.95-8.00 (m, 3H), 8.52 (d, 1H, J=6.41 Hz), 10.9 (d, 1H, J=7.79 Hz), 10.9 (d, 1H, J=7.79 Hz)

[2] Mass spectrometry (ESI-TOF): m/z=561.3055 (M+H)$^+$

[3] UV/Vis spectral analysis: λmax=547 nm

Production Example 9

Production Example of Compound (20)

15.3 mL (40 mmol) of ethyl 4-methoxybenzoylacetate and 0.7 g (6.4 mmol) of sodium carbonate were suspended in 40 mL of 1,2-dichlorobenzene of 14 g (40 mmol) of 1,4-dibutylaminoanthracene-9,10-dione, and the suspension was stirred at 175° C. for 24 hours. After the reaction was completed, the reaction solution was cooled to room temperature, and subjected to column chromatography refining (hexane/ethyl acetate) to obtain 4.8 g (yield of 24%) of a compound (20). The solubility in water of the compound at room, temperature and that at 60° C. were measured, and it was found that both were less than 1% in terms of mass percentage.

<Result of Analysis of Compound (20)>

[1] $^1$H NMR (400 MHz, CDCl$_3$, Room temperature): δ [ppm]=0.96 (dt, 6H, J=16.6, 7.44 Hz), 1.48 (dq, 4H, J=29.7, 7.48), 1.73-1.81 (m, 4H), 3.41 (dd, 2H, J=11.9, 6.87 Hz), 3.79 (s, 3H), 4.34 (d, 1H, J=44.4 Hz), 6.87 (d, 2H, 9.16 Hz), 7.25 (d, 1H, J=9.62 Hz), 7.35 (t, 1H, J=6.87 Hz), 7.52 (t, 1H, J=7.56 Hz), 7.35 (t, 1H, J=6.87 Hz), 7.52 (t, 1H, J=7.56 Hz), 7.66 (d, 1H, J=9.62 Hz), 7.93 (d, 2H, J=8.70 Hz), 8.01 (d, 1H, J=8.24 Hz), 8.48 (d, 1H, J=6.41 Hz), 10.7 (s, 1H)

[2] Mass spectrometry (ESI-TOF): m/z=509.2389 (M+H)$^+$

[3] UV/Vis spectral analysis: λmax=555 nm

Production Example 10

Production Example of Compound (21)

The same operation as that in Production Example 9 was performed except that ethyl 4-methoxybenzoylacetate in Production Example 9 was replaced by ethyl benzoylacetate. Thus, 8.5 g (yield of 45%) of a compound (21) was obtained. The solubility in water of the compound at room temperature and that at 60° C. were measured, and it was found that both were less than 1% in terms of mass percentage.

<Result of Analysis of Compound (21)>

[1] $^1$H NMR (400 MHz, CDCl$_3$, Room temperature): δ [ppm]=0.99 (dt, 6H, J=18.3, 7.33 Hz), 1.44-1.58 (m, 4H), 1.80 (dd, 4H, J=14.7, 7.33 Hz), 3.45 (d, 2H, J=5.50 Hz), 4.36 (br, 2H), 7.30 (d, 1H, J=9.62 Hz), 7.37 (t, 1H, J=7.70 Hz), 7.43 (t, 2H, J=7.79 Hz), 7.55 (t, 2H, J=5.72 Hz), 7.70 (d, 1H, J=9.62 Hz), 7.98 (dd, 3H, J=16.9, 7.79 Hz), 8.52 (d, 1H, J=9.62 Hz), 10.8 (s, 1H)

[2] Mass spectrometry (ESI-TOF): m/z=479.2304 (M+H)$^+$

[3] UV/Vis spectral analysis: λmax=556 nm

<Production of Ink>

According to the method described below, the ink according to the present invention and an ink for comparison were produced.

Production Example of Ink (1)

17 parts of the water-insoluble coloring matter compound according to the present invention (1) and 120 parts of styrene were mixed, and put into an Attritor (made by Mitsui Mining Co., Ltd.). The Attritor was operated for 1 hour to obtain an ink according to the present invention (1).

Production Examples of Inks (4), (6), (8) to (10), (14), (15), (20), and (21)

The same operation as that in the Production Example of the above ink (1) was performed except that the water-insoluble coloring matter compound (1) in the Production Example of the above ink (1) was replaced by the water-insoluble coloring matter compound (4), (6), (8) to (10), (14), (13), (20), or (21). Thus, inks (2) to (10) were obtained.

Production Examples of Inks for Comparison (1) to (3)

The same operation as that in the Production Example of the above ink (1) was performed except that the water-insoluble coloring matter compound (1) in the Production Example of the above ink (1) was replaced by a comparative compound (1), (2), or (3) described below. Thus, comparative inks (1) to (3) were obtained Comparative Compound (1)

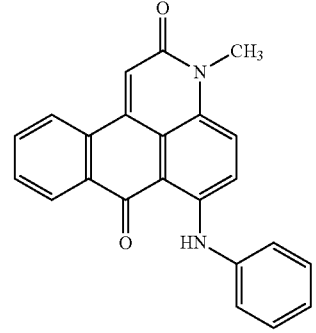

Comparative Compound (2)

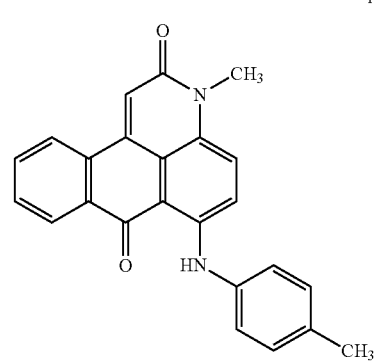

-continued

Comparative Compound (3)

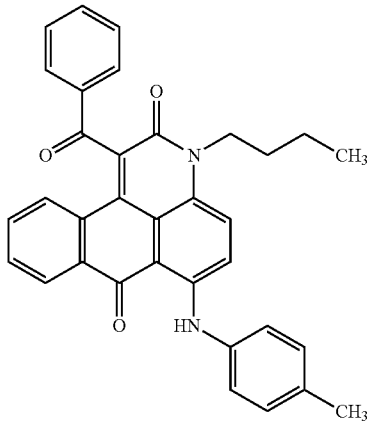

Evaluation

<Evaluation of Solubility of Compound for Solvent>

30 mg of each of water-insoluble coloring matter compounds (1), (4), (6), (8) to (10), (14), (15), (20), and (21) and comparative compounds (1) to (3) was dissolved at room temperature in 0.7 mL of toluene, 0.7 mL of methanol, 0.7 mL of ethyl acetate, and 0.7 mL of chloroform, respectively. These solutions were visually observed, and the solubility of the compound for the solvent was evaluated.

A: completely dissolved (solubility is very good)
B: slightly suspended (solubility is good)
C: not dissolved at all (solubility is bad)

<Measurement of Gamut>

Each of the inks (1), (4), (6), (8) to (10), (14), (15), (20), and (21) and the comparative compounds (1) to (3) was applied onto a contrast ratio measurement sheet by a bar coating method (Bar Nos. 4, 6, 8, 10, 12, 14, 16, 18, and 20), and dried overnight by air to produce an image sample. In each of the image samples, the chromaticity ($L^*$, $a^*$, $b^*$) in the $L^*a^*b^*$ color system was measured by a reflection densitometer SpectroLino (made by Gretag Macbeth GmbH). The chroma ($C^*$) was calculated based on the measured value of color properties by the following equation:

$$C^* = \sqrt{(a^*)^2 + (b^*)^2}$$

<Evaluation of Color Tone>

The color tone was evaluated as follows.

It can be said that as the chromaticity is higher in the magenta gamut direction in the same $L^*$, the chromaticity is closer to the magenta chromaticity represented by the Adobe RGB color space. The color tone was evaluated using the values of $a^*$ and $b^*$ at $L^*=50$. $a^*$ and $b^*$ at $L^*=50$ were determined by interpolation from $L^*$, $a^*$, and $b^*$ obtained from each of the above image samples.

A: $a^*$ is not less than 80, and $b^*$ is not more than $-15$ (much closer to the magenta chromaticity)
B: $a^*$ is not less than 60 and less than 80, and $b^*$ is not more than $-15$ (closer to the magenta chromaticity)
C: $a^*$ is less than 60, and $b^*$ is not more than $-15$ (far from the magenta chromaticity)

<Evaluation of Chroma>

The chroma was evaluated as follows.

It can be said that as the chroma $C^*$ in the same amount of coloring agent per unit area is higher, the lightness and the chroma are higher. The chroma was evaluated using the chroma $C^*$ when the image sample was produced by the above bar coating method (Bar No. 10).

$C^*$ is calculated by the above equation.

A: $C^*$ is not less than 80 (lightness and chroma are very high)
B: $C^*$ is not less than 70 and is less than 80 (lightness and chroma are high)
C: $C^*$ is less than 70 (lightness and chroma are low)

The results of evaluation of Examples and Comparative Examples are summarized in Table 2.

TABLE 2

| | | Solubility | | | | Evaluation of $a^*/b^*$/color tone at $L^*=50$ | Evaluation of $C^*$/chroma using bar No. 10 |
|---|---|---|---|---|---|---|---|
| | Compound | Toluene | Methanol | Ethyl acetate | Chloroform | | |
| Example 1 | (1) | A | A | A | A | 85.2/−20.9/A | 87.7/A |
| Example 2 | (4) | A | A | A | A | 89.1/−28.2/A | 93.4/A |
| Example 3 | (6) | A | A | A | A | 86.6/−20.8/A | 89.1/A |
| Example 4 | (8) | A | A | A | A | 81.6/−28.7/A | 86.5/A |
| Example 5 | (9) | A | A | A | A | 78.3/−30.0/B | 83.9/A |
| Example 6 | (10) | A | A | A | A | 85.3/−22.2/A | 88.2/A |
| Example 7 | (14) | A | A | A | A | 87.4/−26.9/A | 89.1/A |
| Example 8 | (15) | A | A | A | A | 78.7/−26.9/B | 83.2/A |
| Example 9 | (20) | A | A | A | A | 81.6/−28.2/A | 86.3/A |
| Example 10 | (21) | A | A | A | A | 81.4/−28.5/A | 86.2/A |
| Comparative Example 1 | Comparative Compound (1) | C | C | C | B | 40.9/−18.2/C | 44.8/C |
| Comparative Example 2 | Comparative Compound (2) | C | C | C | B | 38.8/−13.4/C | 36.0/C |
| Comparative Example 3 | Comparative Compound (3) | C | C | C | B | 55.7/−32.0/C | 64.2/C |

Apparently from Table 2, it is understood that the water-insoluble compound according to the present invention has high solubility for a solvent and high lightness and chroma, and provides the magenta chromaticity closer to the magenta chromaticity represented by the Adobe RGB color space, Example 11

Production of Magenta Resist Composition

<Production Example of Color Filter (1)>

120 parts of cyclohexanone was mixed with 12 parts of the water-insoluble coloring matter compound according to the present invention (1). The water-insoluble coloring matter compound was dispersed by an Attritor (made by Mitsui Mining Co., Ltd.) for 1 hour. Thus, an ink according to the present invention (11) was obtained.

22 parts of the above ink (11) was slowly added to a solution of 96 parts of cyciohexanone including 6.7 parts of an acrylic copolymerized composition containing n-butyl-methacrylate, acrylic acid, and hydroxyethylmethacrylate in a mass monomer ratio of 40%:30%:30% (weight-average molecular weight of 10,000), respectively, 1.3 parts of dipentaerythritol pentaacrylate, and 0.4 parts of 2-benzyl-2-dimethylamino-1-(4-morpholinophenyl)-butanone(photopolymerization initiator), and the solution was stirred at room temperature for 3 hours. The solution was filtered with a 1.5 μm filter to obtain a magenta resist composition for a color filter (1) according to the present invention.

The above magenta resist composition for a color filter (1) was spin, coated onto a glass substrate, and dried at 90° C. for 3 minutes. The whole surface of the coating was exposed to light, and post-cured at 180° C. to produce a color filter (1).

Examples 12-16

The same operation as that in Example 11 was performed except that the water-insoluble coloring matter compound. (1) in Example 11 was replaced by water-insoluble coloring matter compounds (4), (6), (8), (10) and (21). Thus, resist compositions for color filters (2) to (6) of the present invention were obtained. Moreover, the same operation as that in Example 11 was performed except that, the resist, compositions for color filters (2) to (6) were used. Thus color filters (2) to (6) were produced.

Comparative Examples 4 and 5

The same operation as that in Example 11 was performed except, that the compound (1) in Example 11 was replaced by the comparative compound (1) or (2). Thus, the comparative color filters (1) and (2) were obtained.

Example 17

Preparation of Thermal Transfer Recording Sheet (1)

While a mixed solution of 13.5 parts of the water-insoluble compound according to the present, invention (4) and 45 parts of methyl ethyl ketone/45 parts of toluene was stirred, 5 parts of a polyvinyl butyral resin (DENKA 3000-K; made by DENKI KAGAKU KOGYO KABUSHIKI KAISHA) was gradually added to the mixed solution to obtain an ink according to the present invention (12).

The above ink (12) was applied onto a polyethylene terephthalate film having a thickness of 4.5 μm (Lumirror; made by Toray Industries, Inc.; such that the thickness after drying was 1 μm, and dried to produce a thermal transfer recording sheet (1).

Examples 18-23

The same operation as that in Example 17 was performed except that the water-insoluble coloring matter compound (4) in Example 17 was replaced by water-insoluble coloring matter compounds (1), (6), (8), (10), (14) and (20). Thus, inks for thermal transfer recording (2) to (7) of the present invention were obtained. Moreover, the same operation as that in Example 17 was performed except that the inks for thermal transfer recording (2) to (7) were used. Thus thermal transfer recording sheets (2) to (7) were produced.

Comparative Examples 6 and 7

The same operation as that in Example 17 was performed except that the compound, (4) in Example 17 was replaced by the comparative compound (2) or (3). Thus, comparative thermal transfer recording sheets (2) and (3) were obtained.

<Measurement of Gamut of Color Filter>

The color filter (1) and the comparative color filter (1) above were placed on a contrast ratio measurement sheet, respectively, and the chromaticity (L*, a*, b*) in the L*a*b* color system was measured by a reflection densitometer SpectroLino (made by Gretag Macbeth GmbH). The chroma (C*) was calculated based on the measured value of color properties by the above equation.

<Measurement of Color Tone of Transfer Image>

The thermal transfer recording sheet (1) and the comparative thermal transfer recording sheet (1) above were cut and attached, to a magenta part in an ink cassette for SELPHY CP710 (made by Canon Inc.), respectively, and an image was formed on a dedicated printing paper using a SELPHY CP710 (made by Canon Inc.). The formed images were solid, images of only a magenta color. The respective formed images were a transfer image (1) and a comparative transfer image (1), respectively. In each of the transfer images, the chromaticity (L*, a*, b*) in the L*a*b* color system was measured using a reflection densitometer SpectroLino (made by Gretag Macbeth GmbH). The chroma (C*) was calculated based on the measured value of color properties by the above equation.

<Evaluation of Color Tone>

The color tone was evaluated as follows.

It can be said that as the chromaticity is higher in the magenta gamut direction in the same L*, the chromaticity is closer to the magenta chromaticity represented by the Adobe RGB color space. The color tone was evaluated using the values of a* and b* at L*=50. A sample at L*=50 was formed by controlling the temperature when an image was formed using the SELPHY CP710.

A: a* is not less than 80, and b* is not more than −15 (much closer to the magenta chromaticity)

B: a* is not less than 60 and is less than 80, and b* is not more than −15 (closer to the magenta chromaticity)

C: a* is less than 60, and b* is not more than −15 (far from the magenta chromaticity)

<Evaluation of Chroma>

It can be said that as C* in the same amount of coloring agent per unit area is higher, the lightness and the chroma are higher. The chroma was evaluated using the value of C* wherein the amount of the coloring agent per 25 cm² (5 cm×5 cm) of the color filter and the transfer image was 6.5 mg.

A: C* is not less than 80 (lightness and chroma are very high)

B: C* is not less than 70 and is less than 30 (lightness and chroma are high)

C: C* is less than 70 (lightness and chroma are low)

TABLE 3

| | Compound | Application | Evaluation of a*/b*/color tone at L* = 50 | Evaluation of C*/chroma using bar No. 10 |
|---|---|---|---|---|
| Example 11 | (1) | resist composition (1) | 85.2/−20.9/A | 87.7/A |
| Example 12 | (4) | resist composition (2) | 88.8/−27.2/A | 92.2/A |
| Example 13 | (6) | resist composition (3) | 87.1/−21.0/A | 89.5/A |
| Example 14 | (8) | resist composition (4) | 82.0/−28.3/A | 86.6/A |
| Example 15 | (10) | resist composition (5) | 86.4/−22.0/A | 87.8/A |
| Example 16 | (21) | resist composition (6) | 82.3/−28.1/A | 87.2/A |
| Example 17 | (4) | thermal transfer recording sheet (1) | 89.1/−28.2/A | 93.4/A |
| Example 18 | (1) | thermal transfer recording sheet (2) | 84.8/−20.7/A | 87.2/A |
| Example 19 | (6) | thermal transfer recording sheet (3) | 86.8/−20.5/A | 88.7/A |
| Example 20 | (8) | thermal transfer recording sheet (4) | 82.2/−28.5/A | 86.9/A |
| Example 21 | (10) | thermal transfer recording sheet (5) | 85.9/−23.1/A | 89.1/A |
| Example 22 | (14) | thermal transfer recording sheet (6) | 88.6/−27.1/A | 90.2/A |
| Example 23 | (20) | thermal transfer recording sheet (7) | 82.3/−27.9/A | 86.8/A |
| Comparative Example 4 | comparative compound (1) | comparative resist composition (1) | 40.6/−18.0/C | 44.4/C |
| Comparative Example 5 | comparative compound (2) | comparative resist composition (1) | 38.6/−13.0/C | 40.7/C |
| Comparative Example 6 | comparative compound (2) | comparative thermal transfer recording sheet (1) | 36.5/−10.6/C | 38.0/C |
| Comparative Example 7 | comparative compound (3) | comparative thermal transfer recording sheet (2) | 54.7/−31.1/C | 62.9/C |

Apparently from Table 3, it is understood that the red resist, composition for a color filter and thermal transfer recording sheet obtained using the water-insoluble compound according to the present invention have higher lightness and chroma and provide a magenta chromaticity closer to the magenta chromaticity represented by the Adobe RGB color space than those from the corresponding comparative compound.

INDUSTRIAL APPLICABILITY

The present invention can provide the water-insoluble coloring matter compound having high solubility for a solvent and high lightness and chroma and providing a magenta chromaticity closer to the magenta chromaticity represented by the Adobe RGB color space, and the ink containing the water-insoluble coloring matter compound. Moreover, a film of the water-insoluble coloring matter compound is formed on a substrate to form a coloring material layer. Thereby, a thermal transfer recording-sheet having a good magenta color tone can be obtained. Further, using the water-insoluble coloring matter compound, a resist composition for a color filter having a good magenta color tone can be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-219866, filed Oct. 4, 2011, which is hereby incorporated by reference herein in its entirety.

The invention claimed is:

1. A water-insoluble coloring matter compound represented by formula (1):

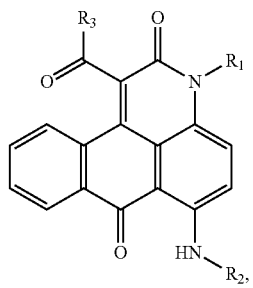

formula (1)

wherein $R_1$ and $R_2$ represent an alkyl group, $R_3$ represents an aryl group, and the alkyl group and the aryl group of $R_1$ to $R_3$ are capable of having a substituent.

2. The water-insoluble coloring matter compound according to claim 1, wherein $R_3$ in the formula (1) is a phenyl group or a 4-methoxyphenyl group.

3. The water-insoluble coloring matter compound according to claim 1, wherein $R_1$ in the formula (1) is a methyl group, a butyl group, or a 2-ethylhexyl group.

4. An ink comprising a water-insoluble coloring matter compound according to claim 1 and a medium.

5. A thermal transfer recording sheet comprising a substrate, and a coloring material layer formed on the substrate by forming a film of a composition containing a water-insoluble coloring matter compound according to claim 1.

6. A resist composition for a color filter comprising a water-insoluble coloring matter compound according to claim 1.

* * * * *